(12) United States Patent
Cai et al.

(10) Patent No.: US 11,155,866 B2
(45) Date of Patent: Oct. 26, 2021

(54) GENE SEQUENCING STRUCTURE, GENE SEQUENCING CHIP, GENE SEQUENCING SYSTEM AND GENE SEQUENCING METHOD

(71) Applicants: BEIJING BOE OPTOELECTRONICS TECHNOLOGY CO., LTD., Beijing (CN); BOE TECHNOLOGY GROUP CO., LTD., Beijing (CN)

(72) Inventors: Peizhi Cai, Beijing (CN); Fengchun Pang, Beijing (CN); Huazhe Liu, Beijing (CN)

(73) Assignees: BEIJING BOE OPTOELECTRONICS TECHNOLOGY CO., LTD., Beijing (CN); BOE TECHNOLOGY GROUP CO., LTD., Beijing (CN)

( * ) Notice: Subject to any disclaimer, the term of this patent is extended or adjusted under 35 U.S.C. 154(b) by 232 days.

(21) Appl. No.: 16/084,670

(22) PCT Filed: Feb. 11, 2018

(86) PCT No.: PCT/CN2018/076265
§ 371 (c)(1),
(2) Date: Sep. 13, 2018

(87) PCT Pub. No.: WO2019/015315
PCT Pub. Date: Jan. 24, 2019

(65) Prior Publication Data
US 2020/0299765 A1 Sep. 24, 2020

(30) Foreign Application Priority Data
Jul. 17, 2017 (CN) .......................... 201710580687.4

(51) Int. Cl.
*C12Q 1/6874* (2018.01)

(52) U.S. Cl.
CPC .................................. *C12Q 1/6874* (2013.01)

(58) Field of Classification Search
None
See application file for complete search history.

(56) References Cited

U.S. PATENT DOCUMENTS

2008/0286762 A1   11/2008   Miyahara et al.
2013/0075793 A1   3/2013    Higuchi et al.
(Continued)

FOREIGN PATENT DOCUMENTS

| CN | 105861294 A | 8/2016 |
| CN | 106497774 A | 3/2017 |

(Continued)

OTHER PUBLICATIONS

Search Report and Written Opinion for International Application No. PCT/CN2018/076265 dated May 9, 2018.

(Continued)

*Primary Examiner* — Xiaoyun R Xu
(74) *Attorney, Agent, or Firm* — Calfee, Halter & Griswold LLP

(57) ABSTRACT

The present disclosure relates to a gene sequencing structure, chip, system, and method. The gene sequencing structure includes: a first electrode and a second electrode spaced apart from each other, a semiconductor layer, a sensing electrode, an insulating layer, and a sensitive film layer. The first electrode is connected to the second electrode via the semiconductor layer, the sensing electrode is in contact with the sensitive film layer, and the insulating layer isolates each of the sensitive film layer and the sensing electrode from each of the first electrode, the second electrode, and the semiconductor layer, wherein the sensitive film layer generates charges in response to receiving ions generated by base pairing during gene sequencing.

18 Claims, 3 Drawing Sheets

(56) References Cited

U.S. PATENT DOCUMENTS

2016/0178569 A1* 6/2016 Hoffman ............ G01N 27/4146
                                                    257/29
2018/0187248 A1    7/2018 Pang et al.
2019/0025242 A1    1/2019 Pang et al.

FOREIGN PATENT DOCUMENTS

CN    106754312 A    5/2017
EP      2581736      4/2013

OTHER PUBLICATIONS

Zhou X. G., Ren L F, Li Y T, et al., The next-generation sequencing technology: A technology review and further perspective, Sci, China Life Science, 2010, 53, doi:10.1007/s11427-010-0023-6.
Search Report from European Application No. 18765347.2 dated Mar. 16, 2021.
Merriman et al., "Progress in Ion Torrent semiconductor chip based sequencing: Nanoanalysis", Electrophoresis, vol. 33, No. 23, Dec. 1, 2021, pp. 3397-3417.

* cited by examiner

GENE SEQUENCING STRUCTURE, GENE SEQUENCING CHIP, GENE SEQUENCING SYSTEM AND GENE SEQUENCING METHOD

RELATED APPLICATION

The present application is the U.S. national phase entry of PCT/CN2018/076265, with an international filing date of Feb. 11, 2018, which claims the benefit of Chinese Patent Application No. 201710580687.4 filed on Jul. 17, 2017, the entire disclosures of which are incorporated herein by reference.

FIELD

The present disclosure pertains to the field of gene sequencing and biological detection, and specifically relates to a gene sequencing structure, a gene sequencing chip, a gene sequencing system and a gene sequencing method.

BACKGROUND

Gene sequencing technology is a commonly used technique in modern molecular biology research. Gene sequencing is capable of analyzing the complete sequence of genes from blood or saliva, and predicting the possibility of suffering from multiple diseases such as cancer or leukemia. Up to now, gene sequencing technology has made considerable progress. The current gene sequencing technology includes the first-generation sanger sequencing technology, the-second generation high-throughput sequencing technology, and the third-generation single-molecule sequencing technology. Currently, the mainstream sequencing technology is still dominated by the second-generation high-throughput sequencing. The single-molecule sequencing technology is still in development and has no substantial commercialization progress.

The second-generation high-throughput sequencing technology mainly includes sequencing-by-synthesis technology, ion semiconductor sequencing technology, ligation sequencing technology and pyrosequencing technology, especially, the sequencing-by-synthesis technology is the mainstream and takes the lead in the market. Both the sequencing-by-synthesis technology and the ligation sequencing technology need to perform fluorescence labeling for bases, and further need to have complex laser sources and optical systems, which complicates the sequencing system, Moreover, labelling reagents are specially expensive, leading to a high sequencing cost and also increasing the sequencing time. The pyrosequencing technology does not require a laser light source and an optical system, but it also needs to perform fluorescence labeling. The ion semiconductor sequencing technology needs to employ CMOS process to produce an ion sensor and two field effect transistors, which are complex in process and different to make.

SUMMARY

Embodiments of the present disclosure provide a gene sequencing structure, a gene sequencing chip, a gene sequencing system, and a gene sequencing method so as to relieve or alleviate the above problems existing in the prior art.

The gene sequencing structure proposed by an embodiment of the present disclosure comprises a first electrode and a second electrode spaced apart from each other, a semiconductor layer, a sensing electrode, an insulating layer, and a sensitive film layer. The first electrode is connected to the second electrode via the semiconductor layer, the sensing electrode is in contact with the sensitive film layer, and the insulating layer isolates each of the sensitive film layer and the sensing electrode from each of the first electrode, the second electrode, and the semiconductor layer, wherein the sensitive film layer generates charges in response to receiving ions generated by base pairing during gene sequencing.

In embodiments of the present disclosure, the gene sequencing structure further comprises a microporous layer above the sensitive film layer, a micropore for accommodating raw materials used during gene sequencing is formed in the microporous layer, and a bottom surface of the micropore is an upper surface of the sensitive film layer.

Further, in some embodiments, a material of the sensitive film layer includes a material that generates charges in response to receiving hydrogen ions. In an example, the material of the sensitive film layer includes silicon nitride.

In some embodiments, the first electrode and the second electrode are located in a same layer of the gene sequencing structure, and the semiconductor layer covers a portion of the first electrode and a portion of the second electrode.

In some embodiments, the semiconductor layer covers a portion of an upper surface of the first electrode and a portion of an upper surface of the second electrode, respectively, and the insulating layer is disposed on a side of the semiconductor layer away from the first electrode and the second electrode.

In some embodiments, the sensing electrode is disposed on a side of the insulating layer away from the semiconductor layer, and an orthographic projection of the sensing electrode on a horizontal plane at least partially overlaps an orthographic projection of the semiconductor layer on the horizontal plane.

In some embodiments, the sensitive film layer is disposed on a side of the sensing electrode away from the insulating layer.

In some embodiments, the first electrode and the second electrode are identical in shape and arranged in mirror symmetry with each other.

In some embodiments, cross sections of the first electrode and the second electrode parallel to a horizontal plane are L-shaped, and L-shaped openings of the first electrode and the second electrode are arranged opposite to each other.

In some embodiments, ends of the first electrode and the second electrode are respectively provided with a connecting line for introducing a test signal.

In some embodiments, a cross-sectional shape of the sensing electrode parallel to a horizontal plane is the same as a cross-sectional shape of the semiconductor layer parallel to the horizontal plane, and an orthographic projection of the semiconductor layer on the horizontal plane falls within an orthographic projection of the sensing electrode on the horizontal plane.

In some embodiments, the micropore has a size ranging from 1 to 100 µm.

Another embodiment of the present disclosure provides a gene sequencing chip comprising a plurality of gene sequencing structures as described in any of the foregoing embodiments.

In some embodiments, the plurality of gene sequencing structures are arranged in an array on a glass substrate.

In some embodiments, ends of the first electrode and the second electrode in each of the gene sequencing structures are respectively provided with a connecting line for introducing a test signal, wherein connecting lines of the first electrodes in the gene sequencing structures located in a same row or a same column are connected to a first test pad located on a periphery of the array of the gene sequencing structures, respectively, and connecting lines of the second electrodes in the gene sequencing structures located in a same row or a same column are connected to a second test pad located on the periphery of the array of the gene sequencing structures, respectively.

A further embodiment of the present disclosure provides a gene sequencing system comprising the gene sequencing chip as described in the foregoing embodiments and a test instrument detachably connected to the gene sequencing chip.

In some embodiments, the test instrument is configured to load a test signal to the first electrode and the second electrode of the gene sequencing chip via a flexible printed circuit, or load a test signal to the first electrode and the second electrode of the gene sequencing chip via a probe of the test instrument.

Yet another embodiment of the present disclosure provides a gene sequencing method based on the gene sequencing structure as described in any of the foregoing embodiments of the gene sequencing structure, comprising: placing a single DNA strand to be detected at a bottom of the micropore; applying a voltage to the first electrode or the second electrode; adding four kinds of deoxyribonucleotides to the micropore successively; detecting whether a current is generated in a loop including the first electrode, the semiconductor layer, and the second electrode to determine a base type on the single DNA strand to be detected according to a deoxyribonucleotide added when a current is generated.

DETAILED DESCRIPTION

Figure 1:
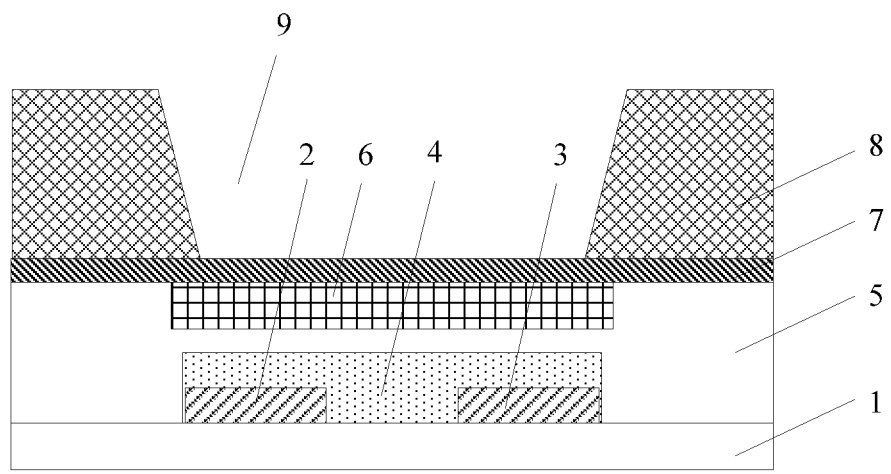
FIG. 1 is a sectional view of a gene sequencing structure provided by an embodiment of the present disclosure.

In order to enable those skilled in the art to better understand the technical solutions of embodiments of the present disclosure, the gene sequencing structure, the gene sequencing chip, the gene sequencing system and the gene sequencing method provided by embodiments of the present disclosure are further described in detail below with reference to the accompanying drawings.

In the description below, the following reference numerals may be used:
1—glass substrate; 2—first electrode; 3—second electrode; 4—semiconductor layer; 5—insulating layer; 6—sensing electrode; 7—sensitive film layer; 8—microporous layer; 9—micropore; 10—single DNA strand to be detected; 11—pairing base; 101—gene sequencing structure; 102—connecting line.

With respect to the problem that the current gene sequencing method generally needs an optical system and fluorescence labelling for bases, which leads to a high gene sequencing cost, an embodiment of the present disclosure provides a gene sequencing structure, which has a simple structure and is beneficial for reducing the cost of gene sequencing.

According to an embodiment of the present disclosure, the gene sequencing structure comprises a first electrode and a second electrode spaced apart from each other, a semiconductor layer, an insulating layer, a sensing electrode, and a sensitive film layer. The first electrode is connected to the second electrode via the semiconductor layer, the sensing electrode and the sensitive film layer are in contact with the insulating layer, and the insulating layer isolates each of the sensitive film layer and the sensing electrode from each of the first electrode, the second electrode and the semiconductor layer. The sensitive film layer is configured to generate charges in response to receiving ions generated by base pairing during gene sequencing.

The gene sequencing structure provided by an embodiment of the present disclosure may be the smallest functional unit in a gene testing chip or a gene testing element. During gene sequencing, corresponding ions are usually generated. For example, when a sample gene is being paired with an added nucleotide, hydrogen ions may be released and can sense charges on a surface of the sensitive film layer, thereby generating an electric potential on the sensing electrode. In case the sensing electrode has no electrical potential, the semiconductor layer (including a p-doped semiconductor and an n-doped semiconductor) in the gene sequencing structure may be substantially in a non-conductive state. When the sensing electrode has an electrical potential in response to receiving ions generated during gene sequencing, the semiconductor layer may be electrically conductive under the effect of the electrical potential. At that time, by applying a test signal to the first electrode and the second electrode, it is possible to detect the fact that the semiconductor layer is electrically conductive under the effect of the electrical potential of the sensing electrode, thereby determining that the sample gene is paired with the added nucleotide, and further realizing gene testing.

The gene sequencing structure proposed by an embodiment of the present disclosure will be described in detail below by way of examples.

As shown in FIG. 1, the gene sequencing structure may comprise a first electrode 2 and a second electrode 3 that are spaced apart from each other; a semiconductor layer 4 that is in contact with the first electrode 2 and the second electrode 3 respectively so as to connect the first electrode 2 to the second electrode 3; an insulating layer 5 that is disposed on a side of the semiconductor layer 4 away from the first electrode and the second electrode; a sensitive film layer 7 that is disposed above the insulating layer 5 and at least includes a sensitive material that generates charges in response to receiving ions generated by base pairing. The gene sequencing structure further comprises a sensing electrode 6 that is in contact with the sensitive film layer 7 and isolated from the first electrode, the second electrode, and the semiconductor layer by the insulating layer 5. The sensing electrode 6 may be disposed on a side of the insulating layer 5 away from the first electrode and the second electrode.

The gene sequencing structure may be integrally arranged above a glass substrate 1. The base pairing is sensed by the sensitive film layer 7 in the gene sequencing structure, so that the gene sequencing structure is simple, which helps to reduce the cost of gene sequencing.

In the example of FIG. 1, the gene sequencing structure may further comprise a microporous layer 8 located above the sensitive film layer 7. A micropore 9 for accommodating raw materials used during gene sequencing is formed in the microporous layer 8, and the bottom surface of the micropore 9 is an upper surface of the sensitive film layer 7. Thus, in performing gene sequencing, raw materials for gene sequencing such as a sample gene, various nucleotides, and the like may be added into the micropore 9.

In some embodiments, the first electrode 2 and the second electrode 3 have the same shape and are arranged in mirror symmetry with each other. Here, the first electrode 2 and the second electrode 3 have the same structure and function, so that there is no need to distinguish between functions when performing gene sequencing, which is convenient for testing.

Figure 2:
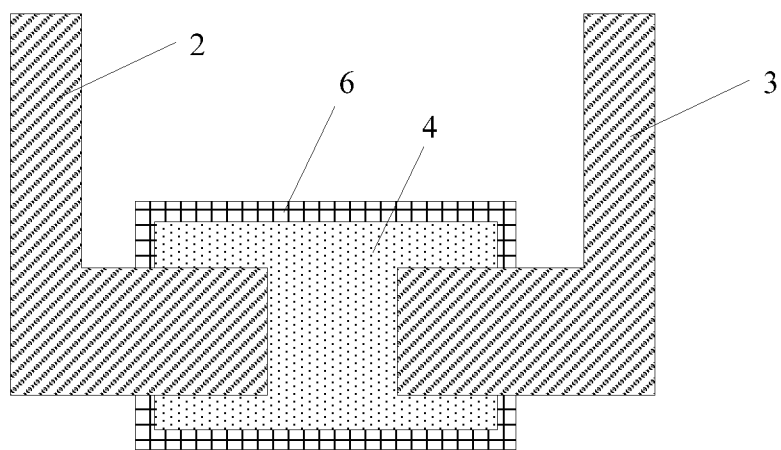
FIG. 2 is a partial top view of the gene sequencing structure shown in FIG. 1.

In some embodiments, as shown in FIG. 2, cross sections of the first electrode 2 and the second electrode 3 parallel to a horizontal plane are L-shaped, and openings of the L-shaped cross sections of the first electrode 2 and the second electrode 3 are arranged opposite to each other. In this way, it is convenient to lead out a test line from a gene testing structure for loading a test signal.

The semiconductor layer 4 may include an a-Si material, a polysilicon material, and so on, and the cross-sectional shape of the semiconductor layer 4 is any one of a square, a rectangle, and a circle to facilitate sensing the presence of ions on the sensitive film layer. Of course, the cross-sectional shape of the semiconductor layer 4 in the gene sequencing structure may also be other shapes, and is not limited by the examples herein. In the gene sequencing structure shown in FIGS. 1 and 2, the first electrode 2, the second electrode 3, the sensing electrode 6, and the semiconductor layer 4 form a structure similar to a top gate thin film transistor, and the semiconductor layer 4 may form a conductive channel where appropriate. For example, when the sensitive film layer generates charges in response to receiving ions generated during gene sequencing so that an electrical potential is generated on the sensing electrode, the semiconductor layer 4 is in a conductive state, and the first electrode 2, the semiconductor layer 4, and the second electrode 3 may form a conductive loop.

In some embodiments, the cross section of the sensing electrode 6 parallel to the horizontal plane has the same shape as the cross section of the semiconductor layer 4 parallel to the horizontal plane, and the orthographic projection of the semiconductor layer 4 on the horizontal plane falls within that of the sensing electrode 6 on the horizontal plane. That is, the area of the orthographic projection of the sensing electrode 6 on the horizontal plane may be greater than or equal to that of the orthographic projection of the semiconductor layer 4 on the horizontal plane. Therefore, the semiconductor layer 4 can be covered by the sensing electrode 6 as much as possible even in the case where the alignment between the sensing electrode 6 and the semiconductor layer 4 is slightly offset in the process of fabricating the gene sequencing structure, so that the semiconductor layer 4 functions satisfactorily to obtain better test results.

In some embodiments, the material forming the sensitive film layer 7 includes a material sensitive to hydrogen ions (H+), that is, a material that generates charges in response to receiving hydrogen ions. Of course, the disclosure does not exclude the cases of forming the sensitive film layer using other sensitive materials that cause voltage variations upon sensing ions generated at the time of base pairing. In one example, the sensitive film layer 7 includes silicon nitride.

In the example of FIG. 1, the micropore 9 is regularly etched on the top of the gene sequencing structure. The micropore 9 in the microporous layer 8 is on the order of micrometers, and has a size ranging from 1 to 100 μm. No limitation is imposed on the shape of the micropore herein, and the size of the micropore refers to the maximum distance between points on the edge of the micropore.

In an embodiment, ends of the first electrode 2 and the second electrode 3 are respectively provided with a connecting line for introducing a test signal. That is, the first electrode 2 and the second electrode 3 are connected to test lines, and connected to an external test instrument via the test lines. In an embodiment, the first electrode 2 and the second electrode 3 may be connected to a test pad respectively using metal leads, and test electrical signals may be loaded by using a flexible printed circuit (FPC), or loaded by directly using a device probe.

Based on the gene sequencing structure described in the foregoing embodiments, when base pairing is taking place, ions (for example, H+) may be released to the sensitive film layer, and the sensitive film layer may generate charges after sensing the presence of H+, thereby causing variations in the electrical potential of the sensing electrode. At that time, the conductivity of the semiconductor layer may change (becoming conductive from non-conductive). Consequently, whether or not base pairing takes place can be determined based on whether or not a change in current occurs in the loop of the first electrode and the second electrode.

At the time of detecting base pairing using the gene sequencing structure, deoxyribonucleotide does not need to be fluorescently labelled, and the laser light source and the optical system are not required, either. Moreover, the gene sequencing structure can be fabricated by means of the manufacturing process for a thin film transistor. Therefore, the cost of gene sequencing and the cost of fabricating gene sequencing products are both relatively low.

Another embodiment of the present disclosure provides a gene sequencing chip comprising a plurality of gene sequencing structures as described in any of the foregoing embodiments. The gene sequencing chip senses base pairing using the sensitive film layer so that the structure of the gene sequencing chip is simple, and the cost of gene sequencing is reduced.

Figure 3:
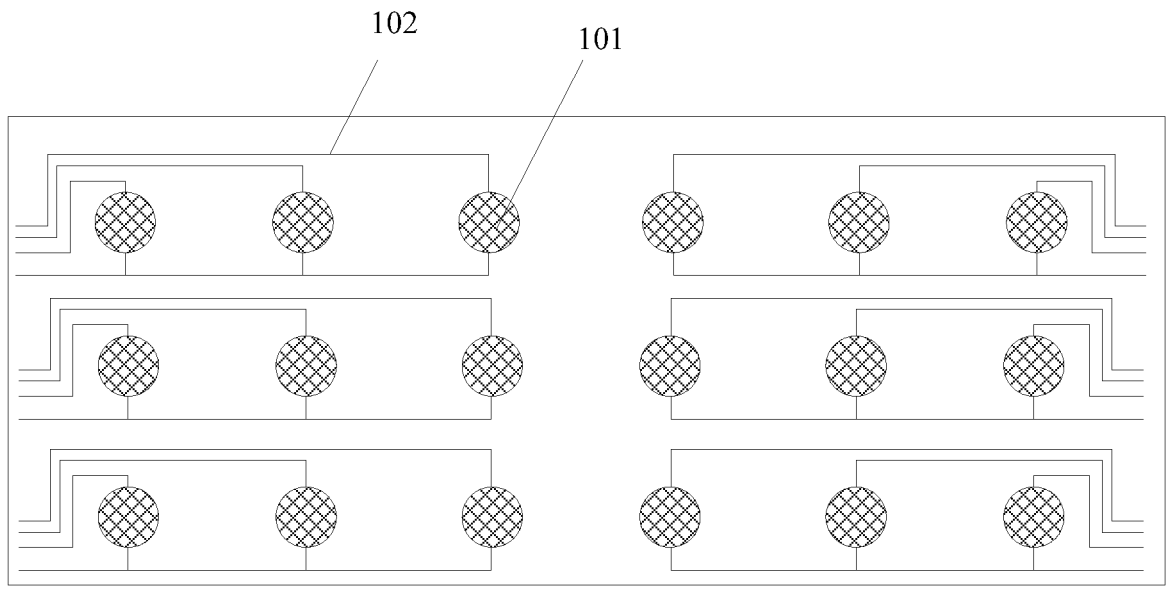
FIG. 3 is a top view of a gene sequencing chip provided by an embodiment of the present disclosure.

As shown in FIG. 3, in some embodiments, a plurality of gene sequencing structures 101 are arranged in an array on a glass substrate. The plurality of gene sequencing structures 101 may also be uniformly distributed on the glass substrate. Of course, the plurality of gene sequencing structures 101 may also be distributed in other ways, which is not limited herein.

In embodiments of the gene sequencing chip having a plurality of gene sequencing structures 101, connecting lines 102 of the first electrodes 2 in the gene sequencing structures 101 located in the same row or the same column may be connected to a first test pad located on the periphery of the array of gene sequencing structures, respectively. Connecting lines 102 of the second electrodes 3 in the gene sequencing structures 101 located in the same row or the same column may be connected to a second test pad located on the periphery of the array of gene sequencing structures, respectively. An external measuring instrument can apply a test electrical signal to the first electrode or the second electrode via the first test pad and the second test pad. In this way, it is advantageous for reducing the space of the gene sequencing chip and obtaining better test efficiency.

A further embodiment of the present disclosure provides a gene sequencing system, which can greatly reduce the time and cost of gene sequencing and improve the efficiency of gene sequencing.

The gene sequencing system comprises a gene sequencing chip and a test instrument detachably connected to the gene sequencing chip. The gene sequencing chip may be the gene sequencing chip as described in the foregoing embodiments.

The test instrument may load a test signal to the first electrode and the second electrode of the gene sequencing chip via a flexible printed circuit, or load a test signal to the first electrode and the second electrode of the gene sequencing chip with a probe thereof. Here, the manner in which a signal is loaded is not limited by embodiments of the present disclosure.

An embodiment of the present disclosure further provides a gene sequencing method based on a gene sequencing structure, which is based on the gene sequencing structure as described in the foregoing embodiments of the present disclosure, so that the cost of gene sequencing is greatly reduced.

Figure 4:
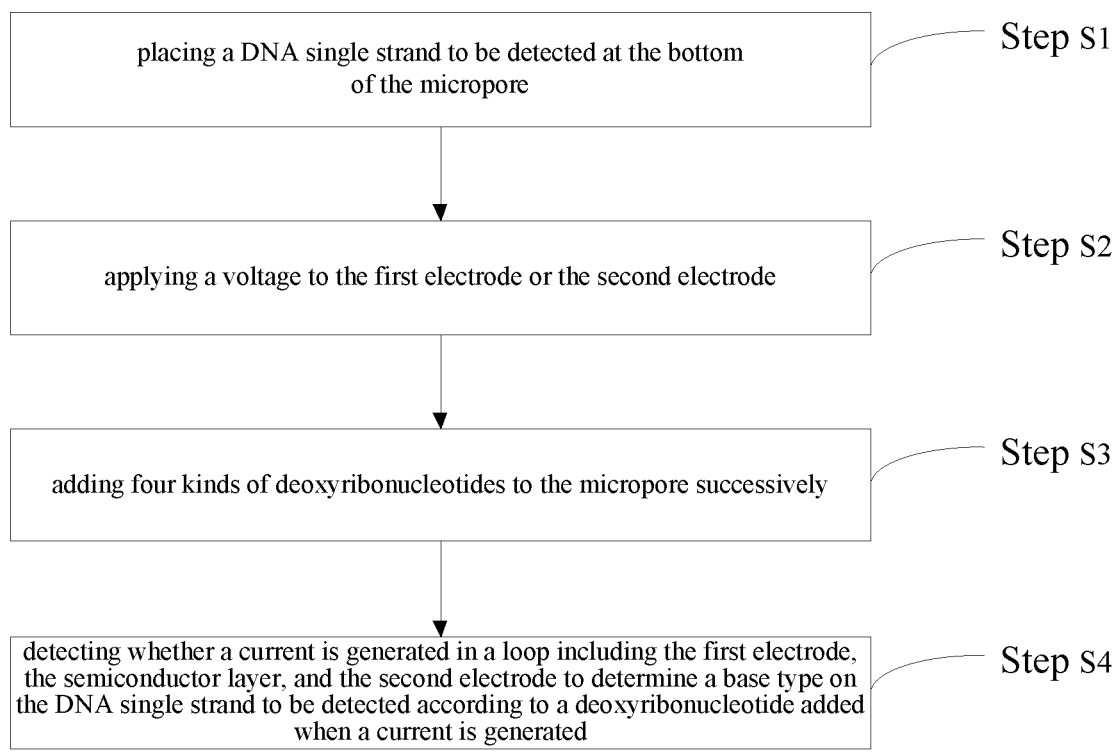
FIG. 4 is a flow chart of a gene sequencing method provided by an embodiment of the present disclosure.
Figure 5A:
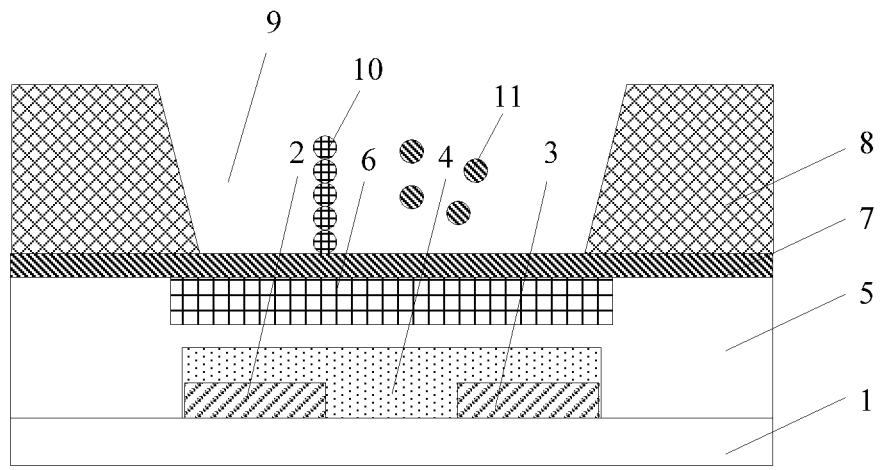
FIG. 5A is used to illustrate the principle of the gene sequencing method provided by an embodiment of the present disclosure

As shown in FIG. 4, the gene sequencing method comprises the steps of:

Step S1): placing a single DNA strand to be detected at the bottom of the micropore. As shown in FIG. 5A, the single DNA strand 10 to be detected is immobilized at the bottom of the micropore 9.

Step S2): applying a voltage to the first electrode or the second electrode. For example, a voltage of 0.5 to 20 V may be applied to the first electrode 2. When the sensitive film layer does not generate charges, the semiconductor layer 4 is substantially in an insulating state, and the current between the first electrode 2 and the second electrode 3 is approximately zero. When the sensing electrode 6 has an electrical potential, the conductivity of the semiconductor layer 4 is greatly enhanced, and at that time, a certain current can be detected between the first electrode 2 and the second electrode 3.

Step S3): adding four kinds of deoxyribonucleotides into the micropore successively.

In performing DNA sequencing, four kinds of pairing bases A, T, C and G may be added to the micropore successively, wherein A, T, C and G are four kinds of nucleotides in the DNA strand, wherein A is adenine, T is thymine, C is cytosine, and G is guanine.

Step S4): detecting whether a current is generated in a loop including the first electrode, the semiconductor layer, and the second electrode so as to determine a base type on the single DNA strand to be detected according to the deoxyribonucleotide added when the current is generated.

Figure 5B:
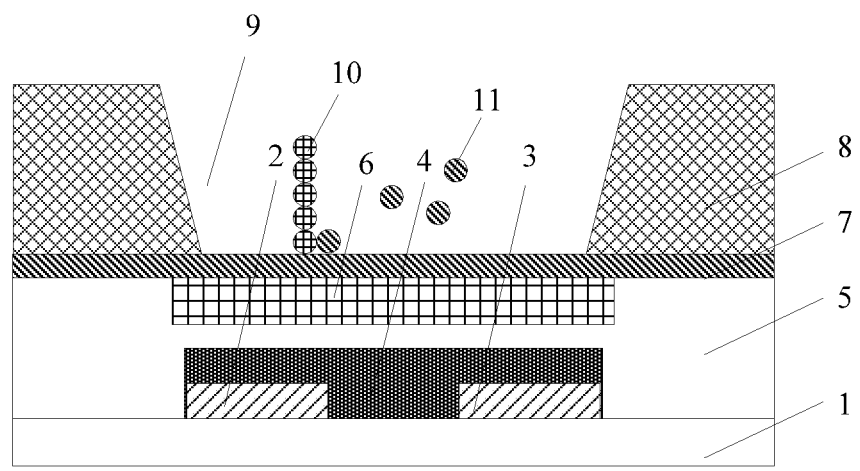
FIG. 5B is used to illustrate the principle of the gene sequencing method provided by an embodiment of the present disclosure.

In one example, as shown in FIG. 5B, when a pairing base 11 is paired with the DNA strand 10 to be detected, hydrogen ions (H+) are released, thereby causing a change in a pH value in the micropore 9. The sensitive film layer 7 at the bottom of the micropore 9 will generate charges after sensing such a change, thereby raising the electrical potential of the sensing electrode 6. After the electrical potential of the sensing electrode 6 is raised, the conductivity of the semiconductor layer 4 is changed (e.g., from an insulating state to a conductive state). In case an external voltage is loaded between the first electrode 2 and the second electrode 3, a current is generated in a loop of the first electrode, the semiconductor layer, and the second electrode. Therefore, when a change in current is detected, it can be determined that a base pairing reaction has taken place, thereby detecting an unknown DNA sequence.

The gene sequencing system and the corresponding gene sequencing method proposed by embodiments of the present disclosure do not need to perform fluorescent labeling for bases, nor do they require the complex laser light source and optical system, thereby greatly reducing the time and cost of sequencing, improving the efficiency, and simplifying the sequencer device.

Based on the gene sequencing structure provided by an embodiment of the present disclosure, when a pairing reaction is being carried out, deoxyribonucleotide does not need to be fluorescently labelled, and the laser light source and the optical system are not required, either. Moreover, the gene sequencing structure can be integrally made by means of the existing manufacturing process for a thin film transistor, so that the cost of the chip is lower. Accordingly, the gene sequencing system and the corresponding gene sequencing method greatly reduce the time and cost of sequencing, improve the efficiency, and simplify the sequencer device.

It can be understood that the above embodiments are exemplary embodiments used only for illustrating the principle of the present disclosure, and that the present disclosure is not so limited. Various variations and improvements may be made by those ordinarily skilled in the art without departing from the spirit and essence of the present disclosure. These variations and improvements are regarded as falling within the scope of the present disclosure.

Other variations to the disclosed embodiments can be understood and effected by those skilled in the art in practicing the claimed invention, from a study of the drawings, the disclosure, and the appended claims. In the claims, the word "comprises" or "comprising" does not exclude other elements or steps, and the indefinite article "a" or "an" does not exclude a plurality. Even though certain features are recited in different dependent claims, the invention also relates to embodiments that collectively include such features. Any reference numeral in the claims should not be construed as limiting.

The invention claimed is:

1. A gene sequencing structure comprising: a first electrode and a second electrode spaced apart from each other, a semiconductor layer, a sensing electrode, an insulating layer, and a sensitive film layer,
   wherein the first electrode is connected to the second electrode via the semiconductor layer, the sensing electrode is in contact with the sensitive film layer, the insulating layer isolates each of the sensitive film layer and the sensing electrode from each of the first electrode, the second electrode, and the semiconductor layer, and the insulating layer is located between the sensing electrode and the semiconductor layer, wherein the sensitive film layer generates charges in response to receiving ions generated by base pairing during gene sequencing,
   wherein the first electrode and the second electrode are identical in shape and arranged in mirror symmetry with each other, cross sections of the first electrode and the second electrode parallel to a horizontal plane are L-shaped, and L-shaped openings of the first electrode and the second electrode are arranged facing each other.

2. The gene sequencing structure according to claim 1, wherein the gene sequencing structure further comprises a microporous layer above the sensitive film layer, a micropore for accommodating raw materials used during gene sequencing is formed in the microporous layer, and a bottom surface of the micropore is an upper surface of the sensitive film layer.

3. The gene sequencing structure according to claim 1, wherein a material of the sensitive film layer includes a material that generates charges in response to receiving hydrogen ions.

4. The gene sequencing structure according to claim 3, wherein the material of the sensitive film layer comprises silicon nitride.

5. The gene sequencing structure according to claim 1, wherein the first electrode and the second electrode are located in a same layer of the gene sequencing structure, and the semiconductor layer covers a portion of the first electrode and a portion of the second electrode.

6. The gene sequencing structure according to claim 1, wherein the semiconductor layer covers a portion of an upper surface of the first electrode and a portion of an upper surface of the second electrode, respectively, and the insulating layer is disposed on a side of the semiconductor layer away from the first electrode and the second electrode.

7. The gene sequencing structure according to claim 6, wherein the sensing electrode is disposed on a side of the insulating layer away from the semiconductor layer, and an orthographic projection of the sensing electrode on a horizontal plane at least partially overlaps an orthographic projection of the semiconductor layer on the horizontal plane.

8. The gene sequencing structure according to claim 7, wherein the sensitive film layer is disposed on a side of the sensing electrode away from the insulating layer.

9. The gene sequencing structure according to claim 1, wherein ends of the first electrode and the second electrode are respectively provided with a connecting line for introducing a test signal.

10. The gene sequencing structure according to claim 1, wherein a cross-sectional shape of the sensing electrode parallel to a horizontal plane is the same as a cross-sectional shape of the semiconductor layer parallel to the horizontal plane, and an orthographic projection of the semiconductor layer on the horizontal plane falls within an orthographic projection of the sensing electrode on the horizontal plane.

11. The gene sequencing structure according to claim 2, wherein the micropore has a size ranging from 1 to 100 μm.

12. A gene sequencing chip comprising a plurality of the gene sequencing structures according to claim 1.

13. The gene sequencing chip according to claim 12, wherein the plurality of gene sequencing structures are arranged in an array on a glass substrate.

14. The gene sequencing chip according to claim 13, wherein ends of the first electrode and the second electrode in each of the gene sequencing structures are respectively provided with a connecting line for introducing a test signal, wherein connecting lines of the first electrodes in the gene sequencing structures located in a same row or a same column are connected to a first test pad located on a periphery of the array of the gene sequencing structures, respectively, and connecting lines of the second electrodes in the gene sequencing structures located in a same row or a same column are connected to a second test pad located on the periphery of the array of the gene sequencing structures, respectively.

15. A gene sequencing system comprising the gene sequencing chip according to claim 12 and a test instrument detachably connected to the gene sequencing chip.

16. The gene sequencing system according to claim 15, wherein the test instrument is configured to load a test signal to the first electrode and the second electrode of the gene sequencing chip via a flexible printed circuit.

17. A method for sequencing a gene with the gene sequencing structure of claim 2, comprising:
    placing a single DNA strand to be detected at a bottom of the micropore;
    applying a voltage to one of the first electrode and the second electrode;
    adding four kinds of deoxyribonucleotides to the micropore successively;
    detecting whether a current is generated in a loop including the first electrode, the semiconductor layer, and the second electrode to determine a base type on the single DNA strand to be detected according to a deoxyribonucleotide added when a current is generated.

18. The gene sequencing system according to claim 15, wherein the test instrument is configured to load a test signal to the first electrode and the second electrode of the gene sequencing chip via a probe of the test instrument.

* * * * *